US008328862B2

(12) United States Patent
Karmarkar et al.

(10) Patent No.: US 8,328,862 B2
(45) Date of Patent: Dec. 11, 2012

(54) MRI COMPATIBLE VASCULAR OCCLUSIVE DEVICES AND RELATED METHODS OF TREATMENT AND METHODS OF MONITORING IMPLANTED DEVICES

(75) Inventors: Parag V. Karmarkar, Columbia, MD (US); Aravind Arepally, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1013 days.

(21) Appl. No.: 12/088,207

(22) PCT Filed: Oct. 4, 2006

(86) PCT No.: PCT/US2006/038932
§ 371 (c)(1),
(2), (4) Date: Oct. 28, 2008

(87) PCT Pub. No.: WO2007/044448
PCT Pub. Date: Apr. 19, 2007

(65) Prior Publication Data
US 2009/0216109 A1 Aug. 27, 2009

Related U.S. Application Data

(60) Provisional application No. 60/724,070, filed on Oct. 6, 2005.

(51) Int. Cl.
*A61F 2/06* (2006.01)

(52) U.S. Cl. ...................... 623/1.15; 600/422

(58) Field of Classification Search .................. 606/200; 600/410, 411, 422, 423, 425, 426, 420; 623/1.15, 623/1.16
See application file for complete search history.

(56) References Cited

U.S. PATENT DOCUMENTS

| | | | |
|---|---|---|---|
| 5,699,801 A | 12/1997 | Atalar et al. | |
| 5,928,145 A | 7/1999 | Ocali et al. | |
| 6,263,229 B1 | 7/2001 | Atalar et al. | |
| 6,533,733 B1 | 3/2003 | Ericson et al. | |
| 6,542,777 B1 | 4/2003 | Griffith et al. | |
| 6,549,800 B1 | 4/2003 | Atalar et al. | |
| 6,575,894 B2 * | 6/2003 | Leysieffer et al. | 600/25 |
| 6,628,980 B2 | 9/2003 | Atalar et al. | |
| 6,675,033 B1 | 1/2004 | Lardo et al. | |
| 6,697,661 B2 | 2/2004 | Raghavan et al. | |
| 6,701,176 B1 | 3/2004 | Halperin et al. | |
| 6,802,857 B1 | 10/2004 | Walsh et al. | |
| 6,885,194 B2 | 4/2005 | Boskamp | |
| 6,898,454 B2 | 5/2005 | Atalar et al. | |
| 7,172,624 B2 * | 2/2007 | Weber et al. | 623/1.16 |
| 2003/0028095 A1 * | 2/2003 | Tulley et al. | 600/422 |

OTHER PUBLICATIONS

Masaryk et al., "Utility of CT angiography and MR Angiography for the Follow-up of Experimental Aneurysms Treated With Stents or Guglielmi Detachable Coils," AJNR AM J. Neuroradiol 2000; 21(8): 1523-1531.

(Continued)

*Primary Examiner* — Victor Nguyen
(74) *Attorney, Agent, or Firm* — Edwards Wildman Palmer LLP; Peter F. Corless; Richard B. Emmons

(57) ABSTRACT

Implantable aneurysm-sac treatment devices include an implantable coil body configured and sized to reside in a sac of an aneurysm. The body has an inductance and capacitance. The capacitance is selected so that the coil resonates at a Larmor frequency of a predefined magnetic field strength.

4 Claims, 25 Drawing Sheets

OTHER PUBLICATIONS

Saatci et al., "CT and MR Imaging Findings and Their Implications in the Follow-up of Patients With Intraranial Aneurysms Treated With Endosaccular Occlusion With Onyx," AJNR AM J Neuroradiol 2003; 24 (4): 567-578.

Schnall et al., "Wireless Implanted Magnetic Resonance Probes for in vivo NMR," Journal of. Mag. Res. 1986; 68:161-167.

International Search Report for International Application No. PCT/US2006/038932.

* cited by examiner

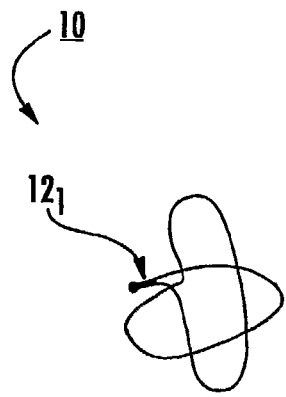
FIG. 16A
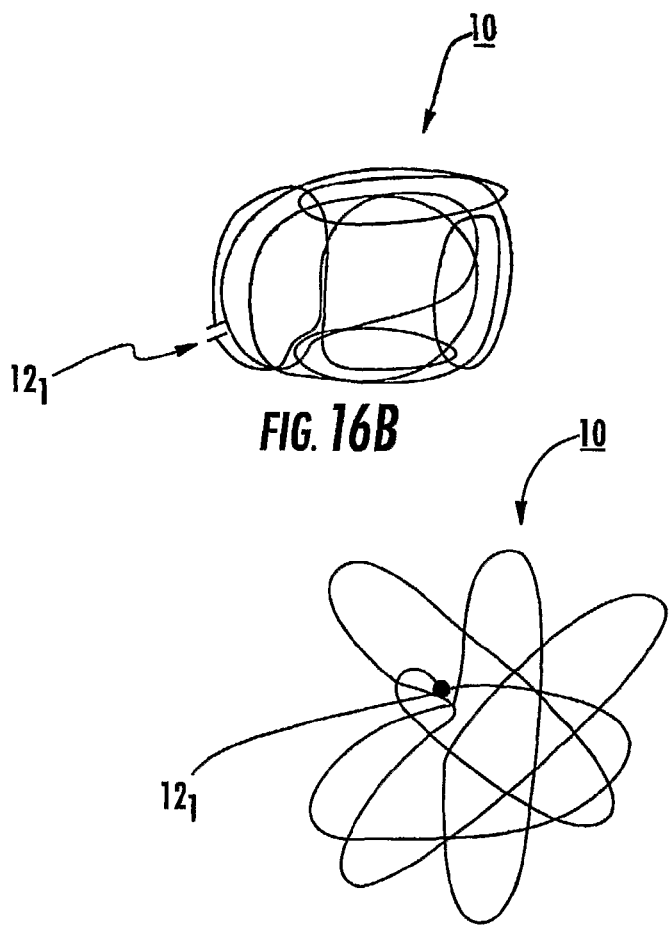
FIG. 16B
FIG. 16C

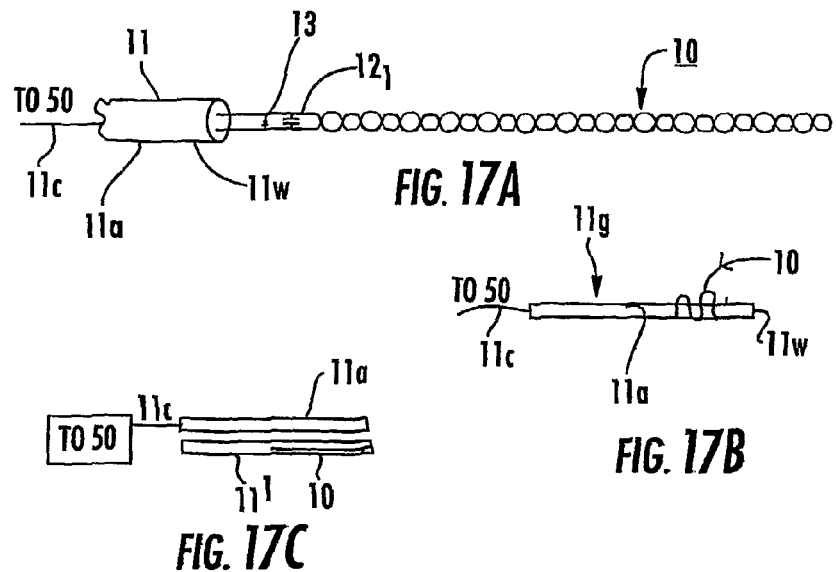
FIG. 17A
FIG. 17B
FIG. 17C
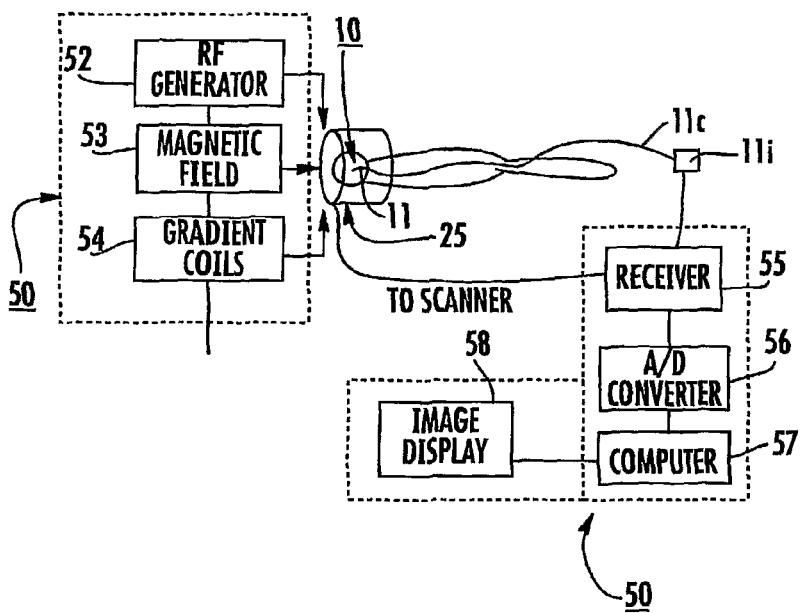
FIG. 17D

MRI COMPATIBLE VASCULAR OCCLUSIVE DEVICES AND RELATED METHODS OF TREATMENT AND METHODS OF MONITORING IMPLANTED DEVICES

RELATED APPLICATIONS

This application is a 35 USC 371 national phase application of PCT/US2006/038932, filed Oct. 4, 2006, and claims the benefit of priority to U.S. Provisional Application Ser. No. 60/724,070, filed Oct. 6, 2005, the contents of which are hereby incorporated by reference as if recited in full herein.

GOVERNMENT FUNDING

This invention was made, in-part, with United States government support under grant number M4006782282 from the National Institutes of Health. The United States government has certain rights to this invention.

FIELD OF THE INVENTION

The present invention relates to interventional and/or monitoring implanted medical devices.

BACKGROUND OF THE INVENTION

Intracranial and peripheral aneurysms have conventionally been treated by percutaneous or endovascular implantation of vascular occlusive material such as devices, fluid or other materials that are placed in the aneurysms before rupture (or sometimes on rupture). For example, generally stated, endovascular treatment of brain or peripheral aneurysms can involve insertion of a catheter (small plastic tube) into the femoral artery in the patient's leg. The catheter is navigated through the vascular system, into the aneurysm. The desired material, device or liquid, is then implanted into the aneurysm.

Examples of implantable devices and materials include microcoils (spirals and framing coils) and/or liquid embolics. Two particular types of devices used to treat intracranial aneurysms are mechanical detachable spirals (MDS) and Guglielmi detachable coils (GDC). The liquid embolic materials are mainly polymeric biomaterials and are injected directly into the aneurysms sacs. An example of a liquid embolic is a cyanoacrylate liquid embolic agent.

The detachable implantable coils are used in procedures known as "aneurysm coiling" which has become a relatively routine clinical procedure. For the aneurysm coiling procedure, miniaturized platinum coils are threaded through the catheter and deployed into the aneurysm, blocking blood flow into the aneurysm and preventing rupture. The coils are made of platinum so that they can be visible via X-ray and are sufficiently flexible to conform to the aneurysm shape. The endovascular coiling, or filling, of the aneurysm is called "embolization" and can be performed under general anesthesia or light sedation. It is said that more than 125,000 patients worldwide have been treated with detachable platinum coils.

Notwithstanding the above, it is believed that in greater than about 15% of cases, aneurysms treated with implanted devices and/or materials may undergo recanalization leading to aneurysm recurrence. To monitor the potential risk of aneurysm recurrence and/or recanalization, patients with microcoils or other types of vascular occlusive treatment types may need relatively frequent follow-up evaluations. The follow-up evaluations typically employ digital subtraction angiography (DSA) taken at about 6 months post-implantation with subsequent MRI (Magnetic Resonance Imaging) being obtained at about every 6 months for several years, typically for about three to five years.

Unfortunately, the follow-up MRIs of patients with coiled intracranial aneurysms are often inadequate and have limited utility for diagnostic purposes. This limitation may be related to coil-generated artifacts that mimic residual flow within the coiled aneurismal cavity. CT imaging can suffer from image distortion secondary to beam hardening artifacts related to microcoils, and therefore, may provide little useful information about aneurysm recanalization. See, e.g., Masaryk et al., *Utility of CT angiography and MR angiography for the follow-up of experimental aneurysms treated with stents or Guglielmi detachable coils*, AJNR Am J Neuroradiol 2000; 21(8): 1523-1531. DSA remains the gold standard for follow-up diagnosis in patients with coiled-intracranial aneurysms. However, DSA is considered an invasive procedure and can carry a small but significant risk of neurological complications.

MRI is considered by some researchers to be the only noninvasive follow-up modality that may be used effectively for monitoring intracranial aneurysms. See, for example, Masaryk et al., cited above, and Saatci et al., *CT and MR imaging findings and their implications in the follow-up of patients with intracranial aneurysms treated with endosaccular occlusion with onyx*, AJNR AM J Neuroradiol 2003; 24 (4): 567-578.

Despite the foregoing, there remains a need to improve MRI data obtained for evaluation of patients with intracranial or peripheral aneurysms, particularly for those patients having implanted vascular occlusive materials and/or devices.

SUMMARY OF EMBODIMENTS OF THE INVENTION

Embodiments of the present invention are directed to systems, devices, and/or computer program products configured to obtain intracranial MRI data using occlusive devices that also act as RF resonators that allow for improved visualization of aneurysms, intracranial vasculature, and/or implantable therapeutic intracranial occlusive devices and materials.

Some embodiments of the present invention configure implantable occlusion coils with at least one miniature wireless pressure transducer, such as a MicroElectroMechanical Systems ("MEMS") based remotely powered device that can sense/measure internal pressures. These devices can be configured to acquire intra-aneurysm pressure.

Some embodiments are directed to implantable aneurysm-sac treatment devices. The devices include an implantable coil body configured and sized to reside in a sac of an aneurysm. The body has an inductance and capacitance. The capacitance is selected so that the coil resonates at a Larmor frequency of a predefined magnetic field strength.

Other embodiments are directed to vascular occlusion devices that include a plurality of microcoils, at least two of which are configured with a different capacitance that is selected for operation at different magnetic field strengths of high-field MRI systems.

Some embodiments are directed to MRI systems for evaluating an aneurysm in vivo. The systems include: (a) at least one implantable RF resonator configured and sized to reside in an intracranial aneurysm sac in a patient, wherein the at least one RF resonator has a resonant frequency corresponding to an operating frequency associated with magnetic field strength of an MRI scanner system; (b) a body coil in communication with an RF excitation source associated with the MRI scanner system, the body coil disposed on the patient, the body coil being configured to inductively couple with the at least one RF resonator to transmit RF excitation pulses comprising low flip angle pulses, from the RF excitation source inside of and proximate the at least one RF resonator; and (c) a surface coil in communication with the MRI scanner system and the at least one RF resonator, wherein, in operation, the at least one RF resonator picks up local MR signal data and cooperates with the surface coil to amplify local signal data from the RF resonator.

Other embodiments are directed to embolic vascular occlusion devices that include a microcoil configured and sized for implantation in an aneurysm sac; and at least one pressure sensor (that may be a MEMS sensor) held by the microcoil.

Still other embodiments are directed to methods of obtaining image data to guide filling an aneurysm sac with embolic material. The methods include: (a) obtaining MRI signal data from an implantable internal RF resonator disposed proximate an aneurysm sac; and (b) filling the sac with a selected embolic material using the obtained MRI signal data.

In particular embodiments, the obtaining step is carried out in substantially real time during the filling step so that the sac can be filled to a desired level without unduly over or under filling the sac space.

Other embodiments are directed to obtaining image data to guide filling an aneurysm sac with embolic material. The methods include: (a) obtaining MRI signal data from an intrabody RF antenna disposed proximate an aneurysm sac; and (b) filling the sac with a selected embolic material using the obtained MRI signal data.

Other embodiments are directed to methods of monitoring the status of an aneurysm. The methods include obtaining MRI signal data from an internal implanted RF resonator disposed in an aneurysm sac to provide images of the aneurysm sac with sufficient detail to allow a clinician to visualize in the MRI image, the presence or absence of at least one of the following: thrombosis, scarring, recanalization, anatomical or structural changes in the sac and blood flow into the sac.

Some embodiments are directed to methods of using MRI signal data to guide placement of a microcoil in an intracranial aneurysm sac. The methods include: (a) introducing a catheter holding a detachable RF resonator coil into a patient; and (b) obtaining MRI signal data in substantially real-time from the internal RF resonator coil as the RF resonator coil is advanced into an intracranial implantation position in the patient.

Still other embodiments are directed to methods of using MRI signal data to guide placement of embolic material in an aneurysm sac. The methods include: (a) obtaining MRI signal data in substantially real-time from an RF antenna proximate an aneurysm sac in the patient; and (b) introducing embolic material into the aneurysm sac based on images generated from the obtaining step.

The introducing step can include either or both implanting an RF resonator coil into the aneurysm sac and introducing liquid embolic material into the aneurysm sac.

These and other embodiments will be described further below.

BRIEF DESCRIPTION OF THE DRAWINGS

FIGS. 16A-16C are schematics of the RF resonator shown in FIG. 15 in a post-deployment sac implanted configuration according to embodiments of the present invention.

FIG. 17A is a schematic of a catheter and RF resonator configured to provide MRI data for MRI guided implantation according to embodiments of the present invention.

FIG. 17B is a schematic illustration of a guidewire MRI antenna used with an RF resonator according to embodiments of the present invention.

FIG. 17C is a schematic illustration of a dual delivery system used to allow MRI guided image data according to embodiments of the present invention.

FIG. 17D is a schematic of an MRI system and the devices shown in FIGS. 17A-17C according to embodiments of the present invention.

DETAILED DESCRIPTION OF EMBODIMENTS OF THE INVENTION

Figure 1A:
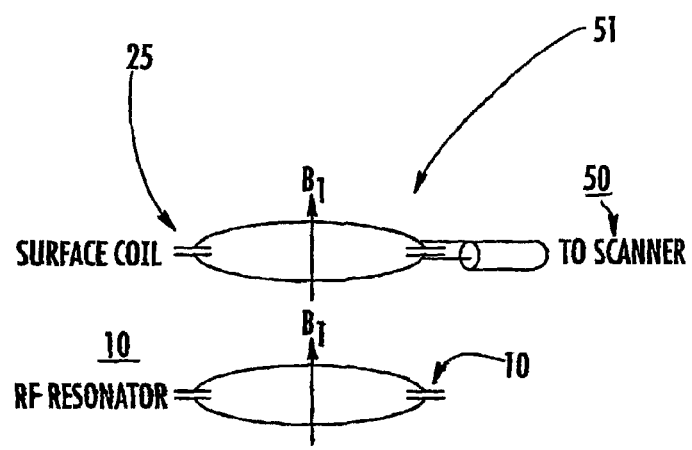
FIG. 1A is a schematic illustration of inductive signal coupling according to embodiments of the present invention.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain antenna embodiment, features or operation of one lead system embodiment can apply to others.

In the drawings, the thickness of lines, layers, features, components and/or regions may be exaggerated for clarity and broken lines illustrate optional features or operations, unless specified otherwise. In addition, the sequence of operations (or steps) is not limited to the order presented in the claims unless specifically indicated otherwise. It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and should not be interpreted in an idealized or overly formal sense unless expressly so defined herein.

Generally stated, embodiments of the present invention are directed to RF resonators configured to reside in an aneurysm sac and provide MRI signal data of local tissue.

The term "RF antenna" refers to a device that is active during at least a receive mode when placed in an MRI system and can receive MRI signal data in vivo, in response to an RF excitation pulse, which can be detected by the MRI system scanner. The term "RF resonator" means that a device is configured to have a harmonic resonance generally corresponding to that of the Larmor Frequency of an MRI system. The harmonic resonance may be a primary or subharmonic resonance. As is well known to those of skill in the art, the Larmor Frequency is field strength dependent. For example, for 1.5T, 3.0T and 6.0T systems, the respective frequencies are 64 MHz, 128 MHz and 256 MHz. It will be appreciated that the internal RF resonator resonance does not need to be exactly that of the system resonance. It is contemplated that the device can be configured to operate with a gain that is about −10 db or less for improved performance.

The term "MRI-visible" means that the device can couple with a transmit (body) coil and a receive (surface) coil, and are "active" during both transmit and receive modes. At certain (typically low) flip angles, the tissue next to the RF resonator(s) is excited. During a receive mode, the RF resonator couples with the surface coils to transmit the detected/received signal from local neural tissue, cells, fluid or matter, to the surface coil. A relatively bright spot on an image corresponds to the location of the RF resonator, but the internal RF resonator itself is typically not visible (see, e.g., FIG. 22). Due to the increased SNR within the RF resonator, a relatively high-resolution image of a space proximate the interior of the RF resonator may be obtained. The image can have reduced pixel size in this region (more signa/voxel). The term "interior" refers to the interior of a boundary or perimeter defined by the at least one RF resonator in the target space.

The term "coil" means that the device has a winding formed with at least one spiral or loop, but typically a series of connected spirals or loops and typically, in a three-dimensional configuration although a two-dimensional loop or spiral configuration may also be employed. The term "small diameter" means the coil is sized to fit in a small aneurysm sac space, typically having a size that is about 1 cm or less, and more typically about 0.5 cm or less. The term "microcoil" refers to miniaturized coils sized and configured for implantation in an aneurysm (sac).

The term "high-field" refers to MRI systems with magnetic fields above about 1.5T, typically between 1.5T and 15T.

The terms "embolic fluid" or "embolic device" means a foreign device or fluid introduced into a sac to substantially occlude an aneurysm to inhibit rupture thereof. The term "filling" describes a process whereby material, fluid and/or devices are introduced into an aneurysm sac to generally, typically, substantially occlude the sac. The embolic device (s) and/or material can substantially conformally fill the sac space. The term "filling" does not require that the entire sac volume be occupied by the foreign material/body. Typically, the sac is filled to the neck without extending beyond the neck boundary into the flow path of the lumen to allow unimpeded blood flow thereat.

The embolic devices and/or fluid can be introduced in any suitable manner, including endovascularly or percutaneously, and may use catheter, cannula, trochar, and/or needle/syringe based delivery or combinations thereof.

It is believed that an underlying primary principle of signal enhancement for MR-visible RF resonators of the instant invention is the inductive signal coupling between RF resonators that are tuned to substantially the same Larmor frequency of an MRI system. A schematic illustration of the mechanism of inductive coupling is shown in FIG. 1A. The inductive coupling was reported as early as 1986 by Schnall et al, *Wireless Implanted magnetic resonance probes for in vivo MRI*, Jnl. Mag. Res. 198; 68: 161-167.

Figure 1B:
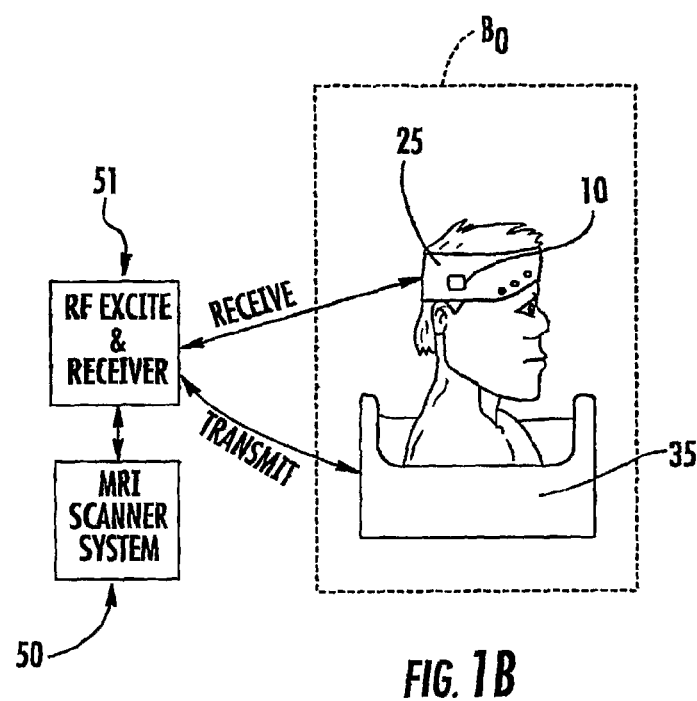
FIG. 1B is a schematic illustration of an MRI system that is configured to acquire MRI image data from an intracranial RF resonator sized and configured for intracranial aneurysm placement as a vascular occlusive device according to embodiments of the present invention.

Generally stated, in operation, the internal RF resonator(s) 10 can function by inductively coupling with a body coil 35 (FIG. 1B) during RF transmit and with a surface imaging coil 25 (FIGS. 1A, 1B) during RF receive modes of the MRI scanner 50 (FIGS. 1A, 1B). FIG. 1B is a schematic illustration of an MRI scanner system 50 that is configured to acquire MRI image data from an intracranial RF resonator sized and configured for intracranial aneurysm placement as a vascular occlusive device according to embodiments of the present invention. MRI scanners are well known to those of skill in the art and include, but are not limited to, TOSHIBA, FONAR, PHILLIPS, SIEMENS and GE MRI systems.

During body coil RF transmit, excitation pulses (typically low flip angles) are multiplied inside and in the vicinity of the RF resonators, resulting in locally increased effective flip angles. The RF excitation may be carried out using low or small flip angle RF excitation pulses. The RF pulses can be transmitted to a surface coil, such as a body coil and/or a head coil. The terms "small" or "low" flip angle refers to flip angles between about 1-55 degrees.

The background gives relatively less signal at the selected excitation angles, resulting in positive contrast between the RF resonator(s) 10 and the background. During RF receive mode, the RF resonator(s) 10 detects and/or picks up the MR signal in its adjacent vicinity, resulting in a B1 field vector that inductively couples to the B1 field vector of the surface coils. The RF receiver coil system 51 (FIG. 1B), which includes the RF resonator(s) 10 and the surface coil 25 act as local signal amplifiers in the region surrounding the RF resonator(s) (FIG. 1A). Thus, microcoils or other configurations designed as RF resonators 10 can inductively couple with the surface coils 25 to provide an SNR increase in the vicinity of (proximate-inside and outside) the coils 10 and may make coils 10 MRI-visible.

Figure 2A:
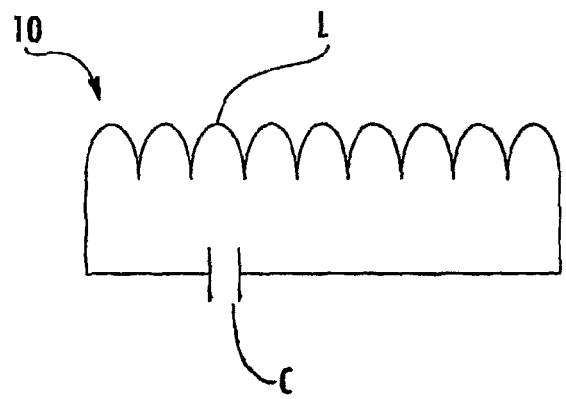
FIGS. 2A and 2B are schematic illustrations of inductive coupling of an RF resonator coil according to embodiments of the present invention.
Figure 2B:
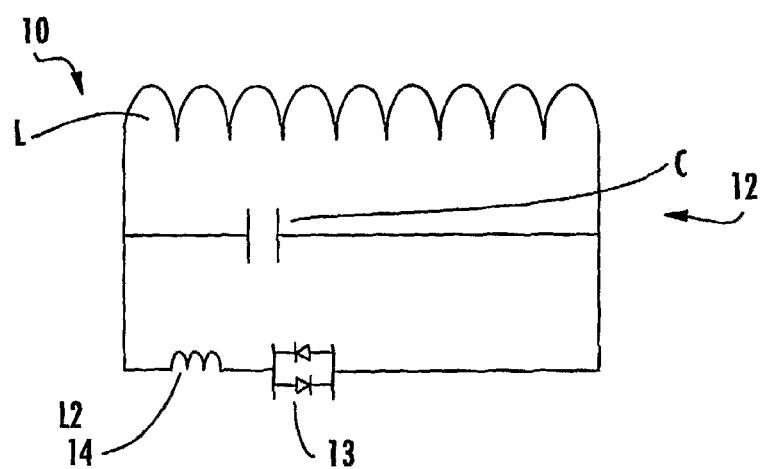

FIGS. 2A and 2B illustrate two optional exemplary electrical diagrams of an RF resonator 10. In each embodiment, the RF resonator 10 is tuned to a Lamor frequency of one or more MRI scanner systems 50 (FIG. 1B). The RF resonator 10 can have an inductance L, typically provided by a twisted wire pair (FIG. 6A) or a coil configuration (FIGS. 4, 5, 6B, 7A-7C, and 8-10) The inductance L can vary depending on the length, coil diameter/type, and the like of the wire used to form the device 10.

As shown, the RF resonator 10 can have a tuned capacitance "C", typically ranging from about 0.01 pF to about 1000 pF. The value of the capacitance will depend on length and other dimensions of the configuration/shape and size of RF resonator 10. The capacitance C can be provided as at least one discrete element 12, such as an MRI compatible semiconductor chip (on a flexible or rigid substrate) held by the RF resonator body at any position thereon. Typically, the semiconductor chip capacitor is non-magnetic and can be held on a silicon substrate or base. In other embodiments, the capacitance C can be created by adjusting the dielectric volume and material between the two wires. Combinations of the capacitance configurations can also be used. If the former, the chip or other capacitor 12 can be laser welded, soldered, brazed or otherwise attached to the device 10.

FIG. 2B also illustrates that a second inductor $L_2$ (14) and opposed parallel diodes 13 can be used to control operation to a "receive" mode making the device 10 generally inactive during a transmit cycle of the MRI system (particularly at certain flip angles). In operation, when greater than a certain current amount is exceeded, the device does not transmit. The device 10 may be configured to "turn on" when there is a certain "turn on" voltage.

Figure 3:
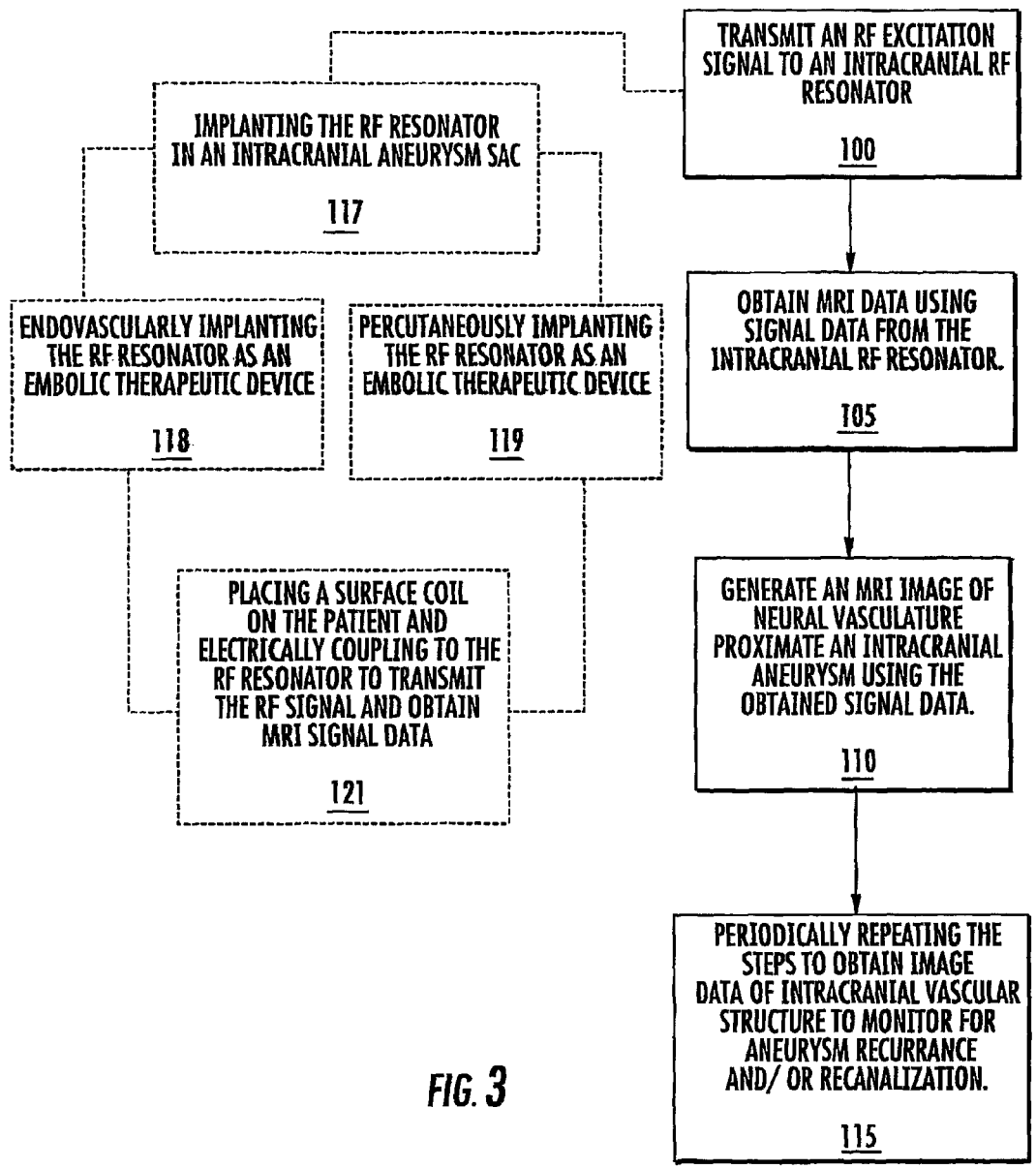
FIG. 3 is a flow chart of operations that can be used to carry out embodiments of the present invention.

FIG. 3 is a flow chart of operations that can be used to carry out embodiments of the present invention. An RF excitation pulse (signal) is transmitted to an intracranial RF resonator (block 100). Typically, the signal comprises low flip angle pulses that are indirectly transmitted to the RF resonator via a body or surface coil. MRI data is obtained using signal data obtained from the intracranial RF resonator (block 105). An MRI image of neural vasculature proximate an intracranial aneurysm is generated using the obtained signal data (block 110). The steps can be repeated periodically to obtain image data of intracranial vasculature structure over time to monitor for recurrence of aneurysm, recanalization or other clinically important features (block 115).

In particular embodiments, the RF resonator is implanted into an intracranial aneurysm sac (block 117) before the transmitting step (block 100). The implanting can be endovascularly carried out to provide the RF resonator as an embolic therapeutic device (block 118) or percutaneously (block 119). A surface (which may be a head) coil can be placed on the patient and electrically coupled to the RF resonator to transmit the RF signal and obtain MRI signal data (block 121).

Embodiments of the instant invention can provide more accurate, detailed and/or precise MRI image data of sac structure, change, contents and/or behavior thereby allowing improved clinical evaluation of the status of the aneurysm. The MRI signal data obtained using the internal-sac based RF resonator(s) 10 may more effectively identify thrombosis, scarring, and/or recanalization. As such, embodiments of the present invention are directed to providing MRI images of aneurysms with improved signal to noise ratio (SNR) proximate the "coiled aneurysms" and the RF resonators 10 can be MRI-visible.

FIGS. 4-8 illustrate various exemplary designs of vascular occlusive RF resonators 10. The RF resonators 10 can be MRI-visible and provide an SNR advantage in the region of the RF resonators 10. The RF resonators 10 typically, but not always include at least one coil formed by a twisted or coiled insulated wire. In the embodiments discussed herein, the reference number "10" will generally refer to the RF resonator. A numerical suffix will be used to identify specific embodiments below (i.e., $10_1$, $10_2$, $10_3$).

The RF resonators 10 can be shaped as microcoils comprising MRI compatible non-ferromagnetic metal such as platinum, gold, Pt—Ir alloy, shape memory allows such as Pt based alloys including, but not limited to Pt—Ni, Pt—Ti, and the like as well as Ni—Ti alloys and the like. The resilient wires forming the inductive portion of the RF resonators 10 can have a width that is between about a 0.001 to about 0.015 inches, and typically between about 0.009 to about 0.038 inches. The resilient wires may typically have a circular cross-section with the width being a diameter dimension. The wires can be electrically insulated from each other and the insulation can be a polymeric dielectric such as polyurethane, nylon, TEFLON, fluoropolymer, polyolefins and the like.

The RF resonator 10 can have a non-coiled (pre-sac) length of between about 1 cm to about 100 cm. The shape of the RF resonators 10 can vary and can be configured to occupy a roughly spherical volume having a spherical diameter of between about 0.1 cm to about 4 cm, and typically, between about 0.5 cm to about 3 cm. The RF resonators 10 can have an implantation shape that is generally linear or more elongated and less wide than the sac configuration. The RF resonators 10 can be pre-configured to automatically take their desired in situ in vivo shape after/during implantation after release from a delivery member. For example, the RF resonators 10 can include long thin wires, which are preshaped into small loops. A 50 cm wire can be compacted into about a 1 cm diameter loop and occupy/fill a relatively small volumetric sac space. Alternatively, the wire forming the coil or RF resonator body can be malleable and shaped in situ as it is introduced into the sac.

The RF resonators 10 can be for transcatheter percutaneous or endovascular delivery. The RF resonator (coils) can be delivered via any suitable delivery mechanism including, but not limited to, detachment/delivery mechanisms such as dielectric/resistance, mediated release, pressure mediated release, laser energy mediated release, chemical reaction mediated release and grasper/holder mediated release.

In some embodiments, the RF resonator 10 can be configured to operate at one or two field strengths, 1.5T, 3.0T, and/or 6.0 T (or other desired field strength). This can allow for compatibility with conventional and future systems. In some embodiments, a plurality of RF resonators 10 can be employed, with at least two configured to resonate at different field strength frequencies. In other embodiments, one or more RF resonators 10 can be used (positioned in the target sac) and each or a plurality can resonate at a plurality of different Larmor frequencies.

Figure 4A:
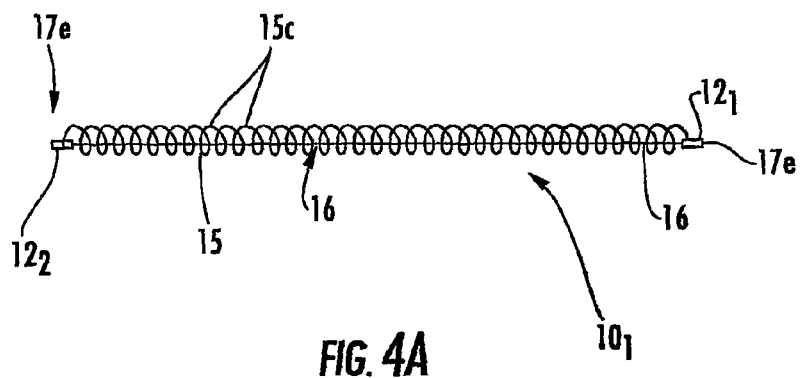
FIG. 4A is a schematic illustration of an exemplary MRI compatible intracranial vascular occlusion device that can operate with enhanced SNR (signal to noise ratio) according to embodiments of the present invention.
Figure 4B:
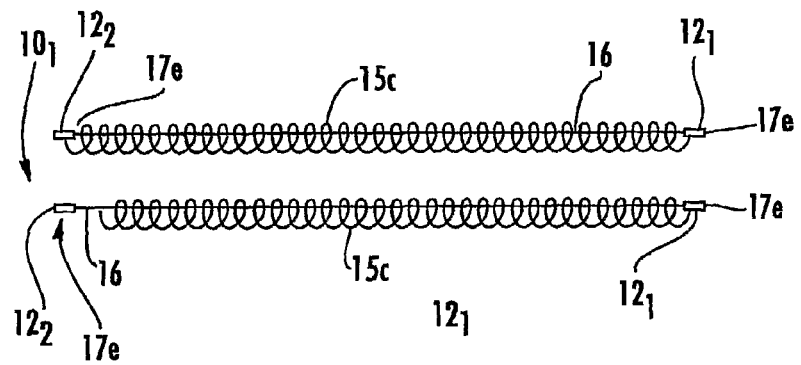
FIG. 4B is a schematic of the device shown in FIG. 4A illustrating that a plurality of coils can form the RF resonator (s) according to embodiments of the present invention.
Figure 5:
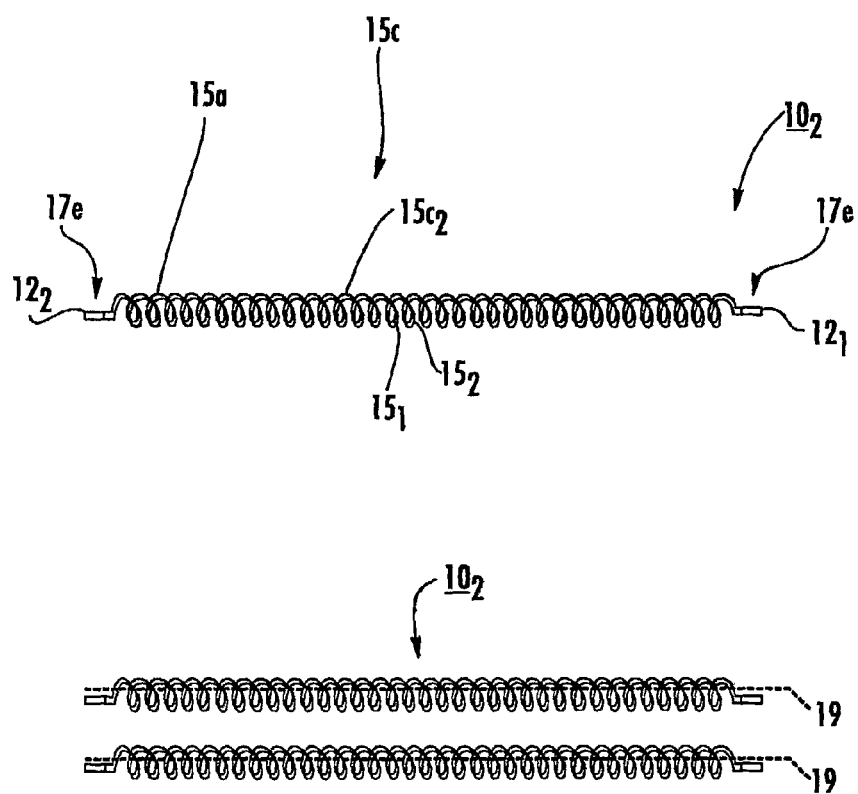
FIG. 5 is a schematic illustration of implantable MRI compatible intracranial vascular occlusion device according to other embodiments of the present invention.

FIG. 4A illustrates an RF resonator 10₁ with an inductor/solenoid coil 15c made of an insulated wire 15 with a central core insulated wire 16 electrically connecting the two end portions 17e of the solenoid coil 15c. The coil 15c is matched and tuned to an MRI frequency via the capacitors 12₁ and 12₂ or either 12₁ or 12₂. FIG. 4B shows that the RF resonator 10 can include multiple resonators 10₁. Multiple coils 15c with multiple respective parallel cores 16 can be assembled in a single design and each coil 15c can be tuned to the same or different frequencies (e.g., 1.5T and 3T MRI frequencies). These resonators 10₁ can be configured so that the coils 15c may be shaped to be deployed concurrently into position via a catheter in an aneurysm to take on a predefined configuration.

FIG. 5A is an RF resonator 10₂ having inductor loop/solenoid coil 15 made of insulated wires 15. The ground 15₁ and the positive 15₂ of the coil 15c are each wound as a solenoid 15c₁, 15c₂ and run in parallel to each other and connected at end portions 17e. The coil 15c is matched and tuned to the desired MRI frequency by capacitors 12₁ and 12₂ or only 12₁ and or only by 12₂. As shown in FIG. 5B, more than one coil 15c can be coiled in various combinations and matched and tuned to different RF frequencies. FIG. 5B also illustrates that coils 15c₁, 15c₂ may optionally be mounted on a core wire/frame wire 19 and the elongate coil length can be preshaped to take on a desired coiled (compressed) implanted configuration in the aneurysm.

Figure 6A:
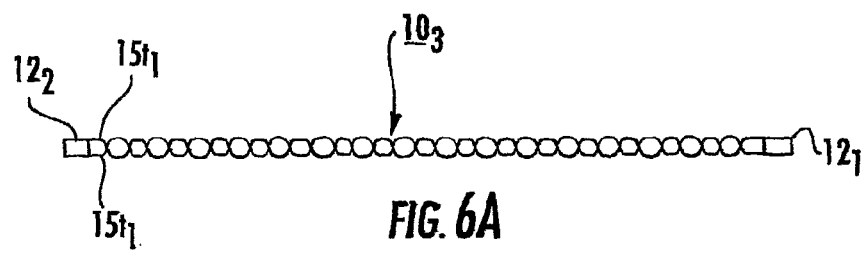
FIG. 6 is a schematic illustration of yet another implantable MRI compatible intracranial vascular occlusion device according to other embodiments of the present invention.
Figure 6B:

FIGS. 6A and 6B illustrate an RF resonator 10₃ that comprises a twisted pair of insulated wires 15t1, 15t2. The resonator 10₃ is matched and tuned to a desired MRI frequency via capacitors 121 and 122 or 121 or 122 only. The twisted pair of wires 15t1, 15t2 can be coiled (FIG. 6B) or uncoiled and can be shaped to be implanted in an aneurysm in a first configuration then take a coiled or more compressed, denser configuration in situ in the sac.

The RF resonators 10 may be shaped in various designs so as to maximize the aneurysm sac filling properties and/or to improve SNR performance (homogeneity and intensity) in the coiled aneurysm. The RF resonators 10 may be configured to define a framing member that receives supplementary embolic sac filling coils or embolic fluid or material. The RF resonators can be "filling coils" configured to cooperate with conventional framing coils. The RF resonators 10 can be configured to provide both a framing member, then the filling members. Different resonator designs may be used and some may resonate in the MRI field strength while others may resonate at different field strengths.

Figure 7A:
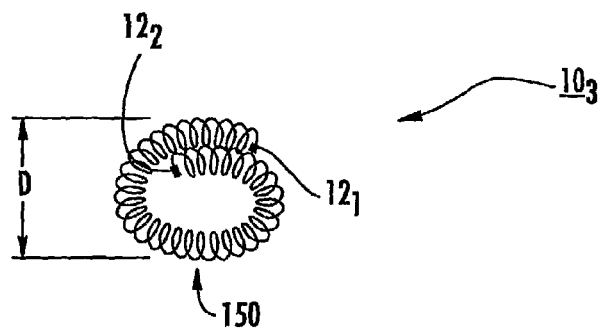
FIGS. 7A-7C are schematic illustrations of an implantable MRI compatible intracranial vascular occlusion device sized and configured to occupy an aneurysm sac according to yet other embodiments of the present invention.
Figure 7B:
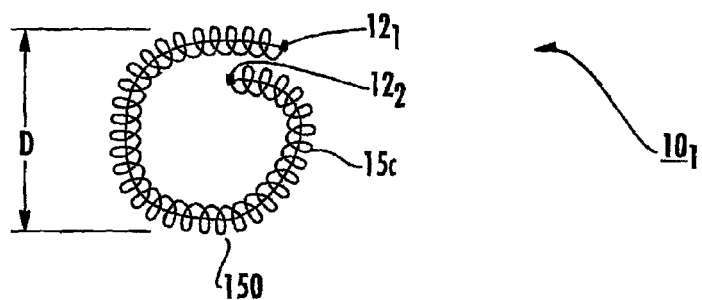
Figure 7C:
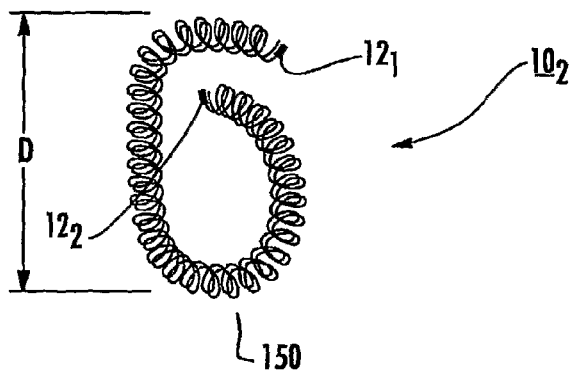

FIGS. 7A-7C illustrate that RF resonators 10 can be configured to spiral or curve to define a substantially spiral coil shape 150 that can occupy at least a portion of a perimeter of the target sac space (typically leaving a center portion open to receive filler material/coils). FIGS. 7A-7C illustrate the RF resonators 10₃, 10₁, 10₂, respectively in a use configuration, each having a coil diameter "D" (taken from the outer edges).

Figure 8:
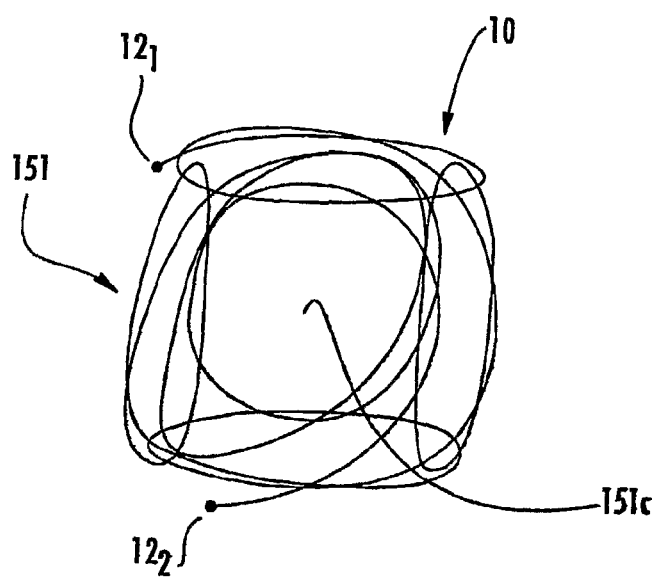
FIG. 8 is a schematic illustration of an implantable MRI compatible intracranial vascular occlusion device sized and configured to occupy an aneurysm sac according to yet other embodiments of the present invention.
Figure 9:
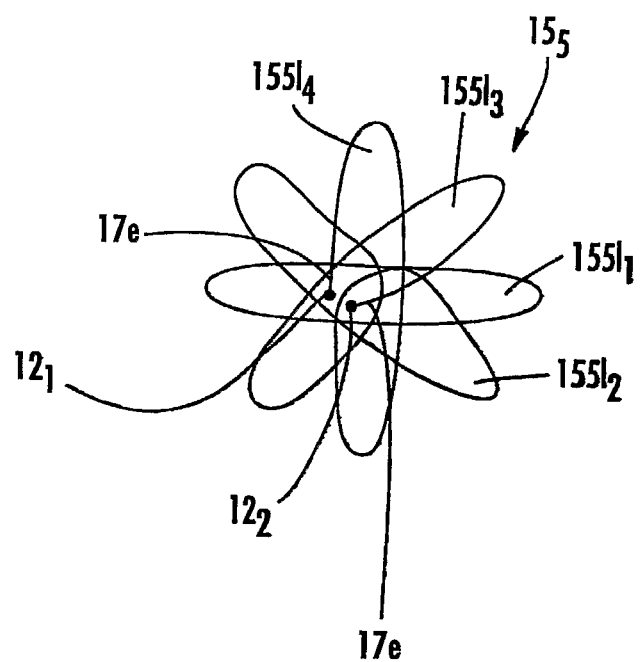
FIG. 9 of an implantable MRI compatible intracranial vascular occlusion device sized and configured to occupy an aneurysm sac according to another embodiment of the present invention.
Figure 10:
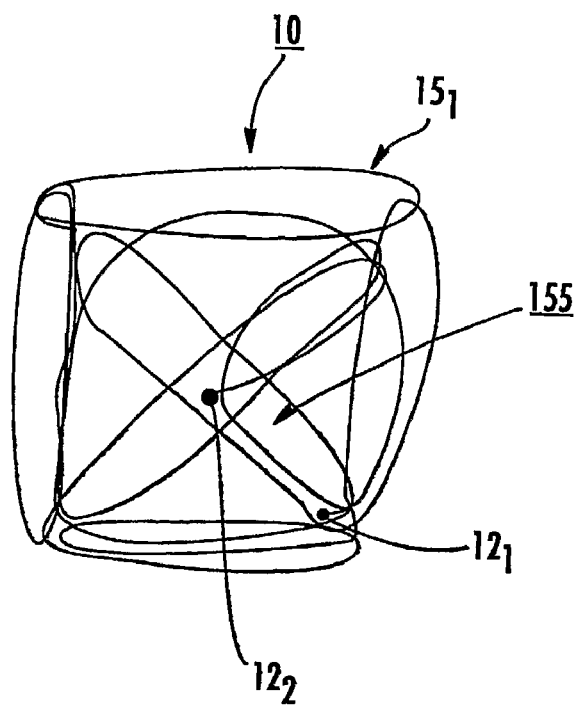
FIG. 10 of an implantable MRI compatible intracranial vascular occlusion device sized and configured to occupy an aneurysm sac according to other embodiments of the present invention.

FIG. 8 illustrates that the RF resonator 10 can be configured to have a generally cubic or box-like coil shape 151 with a generally open center space 151c. FIG. 9 illustrates an RF resonator 10 with a multi-lobe three-dimensional shape 155 configured to occupy a generally spherical space. The lobes 1551₁ ... 1551₄ (more or lesser numbers of lobes may be used) may be symmetrically configured from a common center or non-symmetrical (not shown). A single wire or resonator design 10₁-10₃ noted above may be used to form this shape. The resonator 10 can use one or more capacitors 12₁, 12₂ at the ultimate end portions of the wire (shown as 2, one on each end portion 17e). FIG. 10 illustrates that combinations of the above may be used. As shown, the outer member can be a generally cubic or box-like shape that can be a frame member while the interior can comprise one or more of the multi-lobe coil 155 and/or spiral coils 150 (FIGS. 7A-7C)(the latter not shown for clarity).

Figures 11A, 11B, 11C:
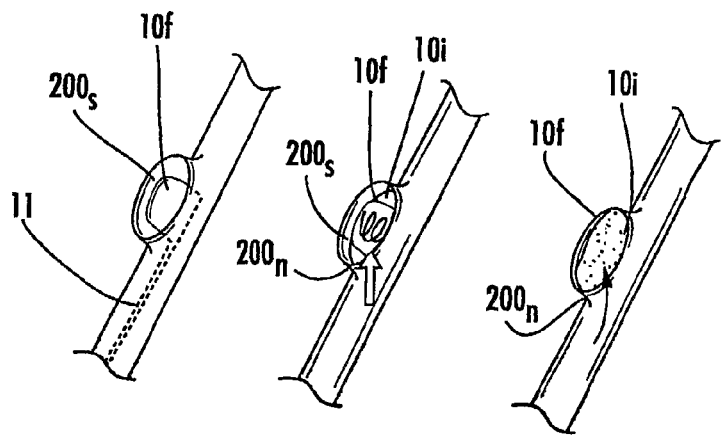
FIG. 11A is a schematic illustration of an MRI compatible RF resonator that can be used to obtain MRI signal data during implantation according to embodiments of the present invention.
FIG. 11B is a schematic illustration of the RF resonator shown in FIG. 11A illustrating that the device can be used to obtain MRI signal data during filling of the aneurysm sac with additional coil filler material according to embodiments of the present invention.
FIG. 11C is a schematic illustration of the RF resonator shown in FIG. 11A illustrating that the device can be used to obtain MRI signal data during filling of the aneurysm sac with additional liquid embolic filler according to embodiments of the present invention.

FIGS. 11A-11C schematically illustrate some embodiments of the present invention. FIG. 11A illustrates that the RF resonator 10 can be configured as a frame member 10f that can be detachably deployed into an aneurysm sac 200s via catheter 11 or other delivery device. Once in position, the frame member 10f can be used to obtain MRI data to monitor the space filling operation. The data can be obtained in substantially real time with sufficient detail to allow a clinician to tailor the filling to the dimensions of the sac to fill the sac 200s up to a neck 200n without under or overfilling the space. FIG. 11B illustrates that the sac space can employ coil filler members 10i while FIG. 11C illustrates that the procedure can inject or introduce embolic fluid into the sac space. The boundaries of the sac space can be monitored via the MRI signal data form the framing member 10f and may also use the coil members 10i, as desired. The filling operation can use embolic fluid as well as internal coils.

Figures 12A, 12B:
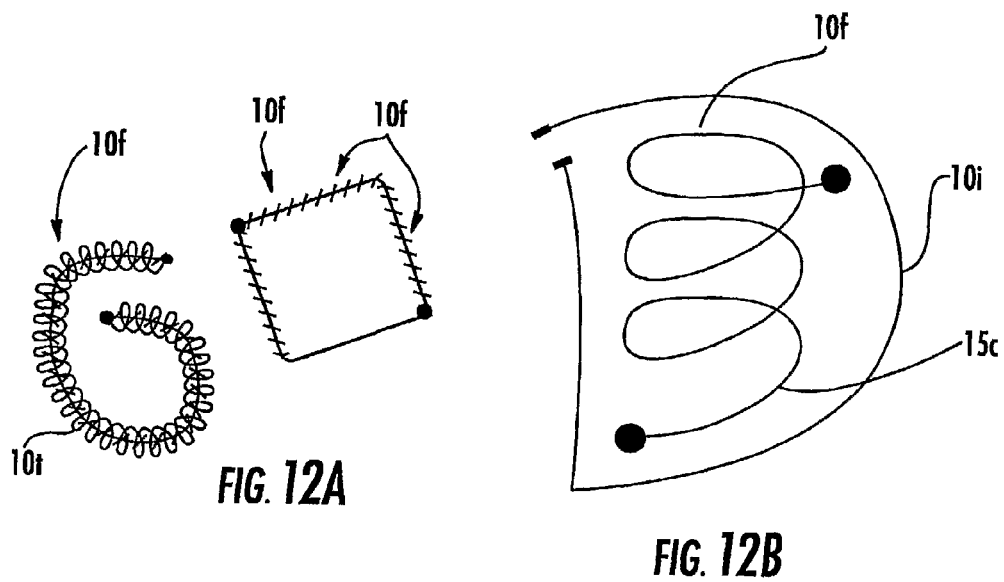
FIG. 12A is a schematic illustration of an RF resonator formed as a sac-framing member, which may optionally include a biocompatible agent to promote tissue in growth according to embodiments of the present invention.
FIG. 12B is a schematic illustration of a conventional framing member (non-MR active) that can be used with RF resonator sac "filler" coils (that may also optionally include a biocompatible agent) to promote tissue growth according to embodiments of the present invention.

FIGS. 12A and 12B illustrate that the framing member 10f (which may be MRI active RF resonators or not) and the internal filler coils 10i (which may also be MRI active RF resonators or not) may be treated or configured to promote tissue in-growth to close off the sac space and inhibit recanalization. A drug coating (timed or heat release and the like) and/or surface treatments, such as fabric, rough surfaces and the like may be employed to promote the desired bioaction/reaction.

Figure 13:
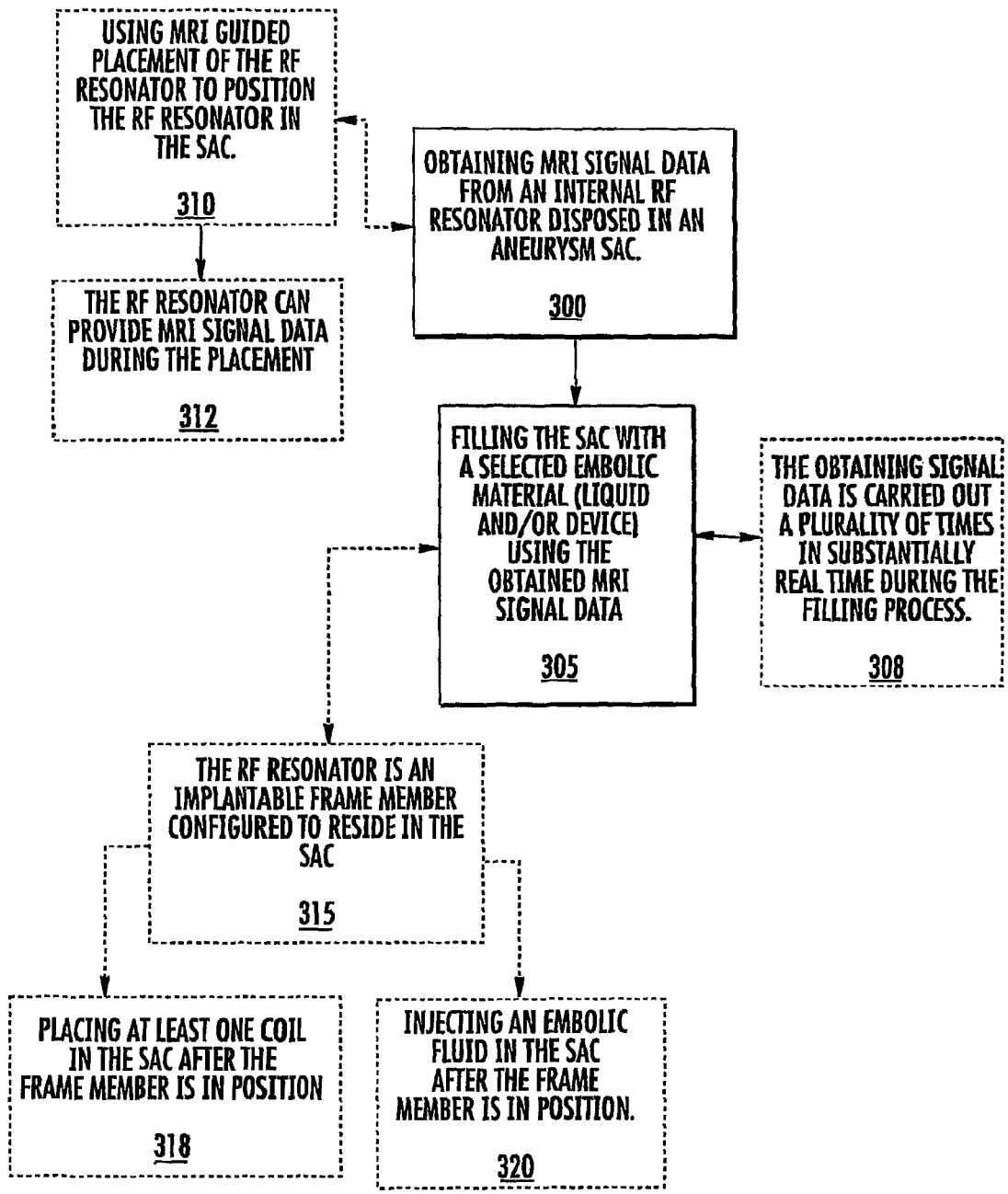
FIG. 13 is a flow diagram of operations that can be used to carry out filling operations using MRI guidance during implantation and/or filling of a sac with an occlusion device/material according to embodiments of the present invention.

FIG. 13 illustrates operations that can be used during implantation of a vascular occlusion device. As shown, MRI signal data can be obtained from an internal RF resonator disposed in an aneurysm sac (block 300). The sac can then be filled with a selected embolic material (fluid and/or device) (block 305). Optionally, the obtaining signal data step can be carried out a plurality of times in substantially real time during the filling process to allow for increased accuracy and/or control of the amount/shape of the filling (block 308).

Optionally, the RF resonator(s) can be implanted or positioned using MRI guided placement to position the RF resonator(s) in the sac (block 310). The RF resonator can provide MRI signal data during the placement (block 312).

Optionally, the RF resonator can be an implantable frame member configured to reside in the sac about a perimeter thereof (block 315). At least one internal coil can be placed in the sac after the RF resonator frame member is in position (block 318) and/or embolic fluid can be injected or inserted into the sac after the RF frame member is in position (block 320). In each situation, MRI signal data from the frame member can be used during the filling process.

Figure 14A:
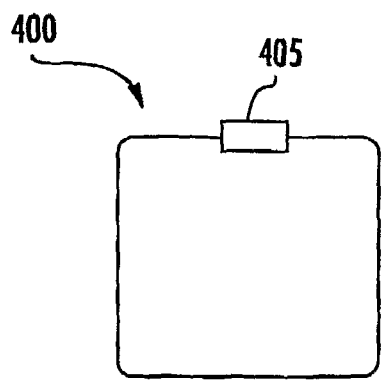
FIG. 14A illustrates a frame member with a wireless pressure transducer according to yet other embodiments of the present invention.
Figure 14B:
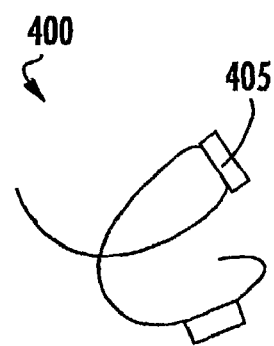
FIG. 14B illustrates a microcoil with at least one pressure transducer according to embodiments of the present invention.
Figure 14C:
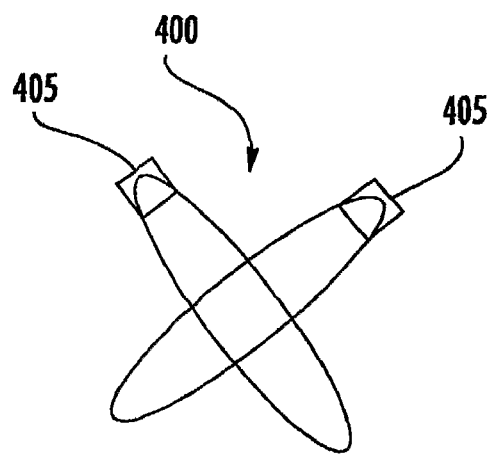
FIG. 14C illustrates a micro coil according to the embodiments of the present invention.

FIGS. 14A-14C illustrate that various vascular occlusion microcoils 400, which may be conventional microcoils or RF resonators 10, can include at least one wireless pressure sensor 405 to allow a clinician to monitor sac pressure either during or after implantation. The pressure sensor 405 can be placed at locations where they are responsive to sac wall pressure, such as at an outer boundary or near the neck of the sac. The pressure sensors 405 are MRI compatible but need not operate in a magnetic field. In operation, at least one pressure reading can be taken at the end of a filling operation (when implantation or the procedure is complete). Subsequent pressure readings can be taken and compared for any non di minimis change over time. A drop or increase in pressure may signal that further evaluation of the sac site is needed.

In some embodiments, the pressure sensor can be a miniaturized pressure transducer. The pressure sensing range can be configured at any suitable range, and may be between about 0-200 mmHg.

In particular embodiments, the pressure sensor can be a MicroElectroMechanical Systems (MEMS) sensor. Issys, Inc., of Ypsilanti, Mich. is one known manufacturer of biomedical MEMS pressure sensors. Examples of technology/devices, which may be suitable for fabrication/configuration of pressure sensors suitable for incorporation into an embolic (aneurysm sac) implant include: U.S. Pat. Nos. 6,824,521; 6,499,354; and 4,881,410, the contents of which are hereby incorporated by reference as if recited in full herein. See also, Massoud-Ansari et. al., *Applications of Dissolved Wafer Process in the Biomedical Field*, MST News, March 1999; K. Najafi, *Integrated sensors in Biological Environments*, Invited Paper, Sensors and Actuators, Vol. B1, 1990; and Ji et al., *An Implantable CMOS circuit interface for multiplexed microelectrode recording arrays*, IEEE Jnl of Solid State Circuits, Vol. 27, No. 3 (March, 1992).

Figure 15:
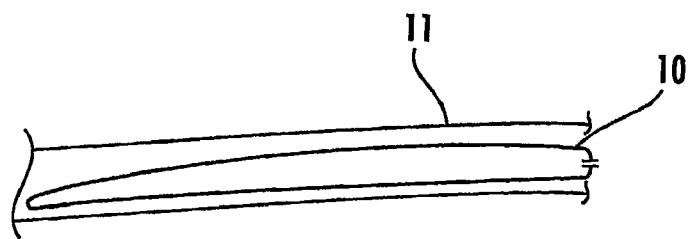
FIG. 15 is a schematic of an RF resonator held by a catheter in an implantation configuration according to embodiments of the present invention.

FIG. 15 illustrates that during deployment or implantation, the RF resonator 10 can be held inside a catheter 11 as a generally linear body. Alternatively, the RF resonator can be wrapped around a catheter or other implant delivery device (not shown). In any event, during deployment, the RF resonator 10 can define an a first shape of an inductor made of shape memory alloy (insulated wire(s)) that is tuned to at least one selected MRI frequency by one or more capacitors at any location along the length of the inductor. The RF resonator 10 wire can take on a second shape, typically a coil shape, when in position in the sac or target space. The coil shape and size can be for framing, filling or a combination of framing or filling the sac. The device 10 can be implanted in the aneurysm sac that takes on a predefined coil shape upon release. The device may be formed by at least two parallel wires, which take the preset shape upon deployment from the catheter 11. FIGS. 16A-16C illustrate exemplary configurations that the RF resonator 10 can take after release from the catheter 11. FIG. 16A illustrates a substantially 2-D planar shape with two lobes and a capacitor 121. FIG. 16B illustrates a framing shape similar to a box or birdcage. FIG. 16C illustrates the RF resonator 10 having a multi-lobe three-dimensional shape and can act as a loop antenna.

In some embodiments, the implantable RF resonator 10 described herein, can be connected to the MRI scanner 50 during implantation to provide high resolution images of the aneurysm sac during filling of the aneurysm with liquid embolics or other medical devices or therapies. The connection can employ a coaxial cable. The connection of the RF resonator 10 and the coaxial cable can be detachable to allow for the RF resonator to deploy into position in the sac. The detachment can be a mechanical, electrical, chemical, light (laser) based connection. In other embodiments, as will be discussed below a separate internal RF antenna can be used (alone or with the above) to provide the high-resolution images of the sac during filling.

FIGS. 17A-17C illustrate devices that can be used to provide MRI guided treatments using image data obtained from either the RF resonator 10 and/or an RF antenna 11a. The RF antenna 11a may be held on a common delivery device with the RF resonator 10 or it may be separate. The RF antenna 11a can be configured to deliver embolic liquid material to the sac. FIG. 17D illustrates an MRI implantation system that is electrically connected to the RF antenna 11a (and/or resonator 10, depending on the type of RF antenna used).

The embodiments shown in FIGS. 17A-17D are directed to systems and devices that provide MRI guided placement of implantable devices in the sac or visualization of the sac for therapeutic procedures/filling. As shown in FIG. 17A, a RF resonator 10 delivery catheter 11 can be configured to function as an RF antenna 11a to obtain and relay signal data to the MRI scanner 50. The catheter 11 can include the coaxial cable as discussed above. The cable is connected to the MRI scanner 50 via lead 11c. The catheter 11 can define one or more lumens, one of which can be used to deliver liquid embolic material into the sac. The RF resonator 10 can remain attached to the catheter 11 during the filling or implanted prior to the filling.

In other embodiments, as shown in FIG. 17B, the RF resonator 10 can be held on a coaxial cable configured as a guidewire 11g that forms the RF antenna 11a. The guidewire 10g may comprise NITINOL or another non-ferromagnetic material having sufficient mechanical strength and rigidity to function as a guidewire to guide the RF resonator 10 to the sac. The guidewire 11g is connected to the lead 11c that extends out of the patient to connect to the MRI scanner 50. As desired, a separate catheter can be used to deliver other embolic material, liquid or devices to the sac. Alternatively, the guidewire 11g can reside outside or inside a catheter.

FIG. 17C illustrates that the RF resonator 10 can be held by a resonator delivery device 11'. The resonator delivery device 11' can be a catheter or guidewire (shown as a catheter in FIG. 17C with the RF resonator 10 held therein). A second device used during the procedure is the RF antenna 11a. The RF antenna 11a is connected to the MRI scanner 50 via lead 11c. The RF antenna 11a can be configured as a catheter or guidewire. Where the RF antenna 11a is configured as a catheter 11, the catheter can be sized with a core that holds the resonator delivery device 11' and resonator 10 therein. The resonator delivery device 11' with resonator 10 can be slidably advanced into the catheter based RF antenna 11a after the catheter-based RF antenna 11a is in position. Alternatively, the resonator delivery device 11' can reside in the catheter-based antenna 11 before implantation or introduction into the body.

Still referring to FIG. 17C, alternatively, where the RF antenna 11a is provided as a guidewire 11g, the RF resonator delivery device 11' can be sized and configured to matably receive the guidewire 11g and slidably advance thereover after the innermost portion of the guidewire 11g is in position proximate the sac.

Examples of RF antennas suitable for the guidewire 11g and/or catheter 11 are described in one or more of U.S. Pat. Nos. 5,699,801; 5,928,145; 6,549,800; 6,628,980; 6,675,033; 6,263,229; 6,701,176, and 6,898,454, the contents of these patents are hereby incorporated by reference as if recited in full herein.

In FIG. 17D, the MRI scanner 50 is schematically shown with well known system components, including an RF Amplifier (generator) 52, Magnetic Field 53, and Gradient coils 54 (and amplifier), and a receiver 55, A/D converter 56, signal processor 57 (computer) and image display 58. The catheter 11 or guidewire 11g has a lead 11c that is configured to connect to the MR scanner 50. This connection may be via an interface 11i. In this way, the RF antenna 11a obtains and transmits MRI signal data to the scanner.

FIG. 17A illustrates that, during implantation, the RF resonator 10 (shown as a twisted wire pair, but the invention is not limited thereto) is held in electrical communication with the RF antenna 11a. The at least one tuning capacitor $12_1$, can tune the RF resonator 10 to the desired RF frequency and a decoupler can be built into the RF resonator 10 upstream of the coaxial cable or at a proximal end or the coaxial cable. As shown, a decoupling diode 13 can be disposed between the coaxial cable and the RF resonator 10. The coaxial cable is connected to the MRI scanner 50 and a high-resolution image of the sac can be obtained. The imaging can be used to guide delivery of additional embolic materials, biologic materials and the like into the aneurysm sac. Once the aneurysm is filled as desired, the implantable RF resonator can be detached from the coaxial cable. The RF resonator 10 can then provide image data by inductive coupling with the surface coils 25 for monitoring, post-implantation.

In some embodiments, MRI signal data provided by the RF antenna 11a and/or the RF resonator 10 (while held by the catheter 11 or guidewire 11g), can be used to guide the filling or preparation of an intracranial or peripheral aneurysm sac.

As shown in FIGS. 17A and 17B, respectively, the catheter 11 or guidewire 11g can be introduced into the patient and can hold a detachable RF resonator coil. As shown in FIG. 17C, a device not holding the RF resonator 10 or not in electrical communication therewith can be used to collect the high resolution signal data. In any event, MRI signal data can be obtained in substantially real-time from the RF antenna 11a and/or the internal RF resonator coil 10 at an aneurysm sac (such as an intracranial loci) position in the patient.

The flowcharts and block diagrams of certain of the figures herein illustrate the architecture, functionality, and operation of possible implementations of the present invention. In this regard, each block in the flow charts or block diagrams represents a step, module, segment, which may form a portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

Some operations can be carried out by data processing systems that may be incorporated in a digital signal processor that may be in communication with the MRI scanner (or be part of the scanner system itself). The processor communicates with memory via an address/data bus. The processor can be any commercially available or custom microprocessor. The memory is representative of the overall hierarchy of memory devices containing the software and data used to implement the functionality of the data processing system. The memory can include, but is not limited to, the following types of devices: cache, ROM, PROM, EPROM, EEPROM, flash memory, SRAM, and DRAM.

The memory may include several categories of software and data used in the data processing system: the operating system; the application programs; the input/output (I/O) device drivers; the Pressure Sensor or RF resonator Operation Modules; and data.

As will be appreciated by those of skill in the art, the operating system may be any operating system suitable for use with a data processing system, such as OS/2, AIX, DOS, OS/390 or System390 from International Business Machines Corporation, Armonk, N.Y., Windows CE, Windows NT, Windows95, Windows98, Windows2000 or other Windows versions from Microsoft Corporation, Redmond, Wash., Unix or Linux or FreeBSD, Palm OS from Palm, Inc., Mac OS from Apple Computer, LabView, or proprietary operating systems. The I/O device drivers typically include software routines accessed through the operating system by the application programs to communicate with devices such as I/O data port (s), data storage and certain memory components.

The present invention is explained in greater detail in the following non-limiting Examples.

EXAMPLES

Figure 18:
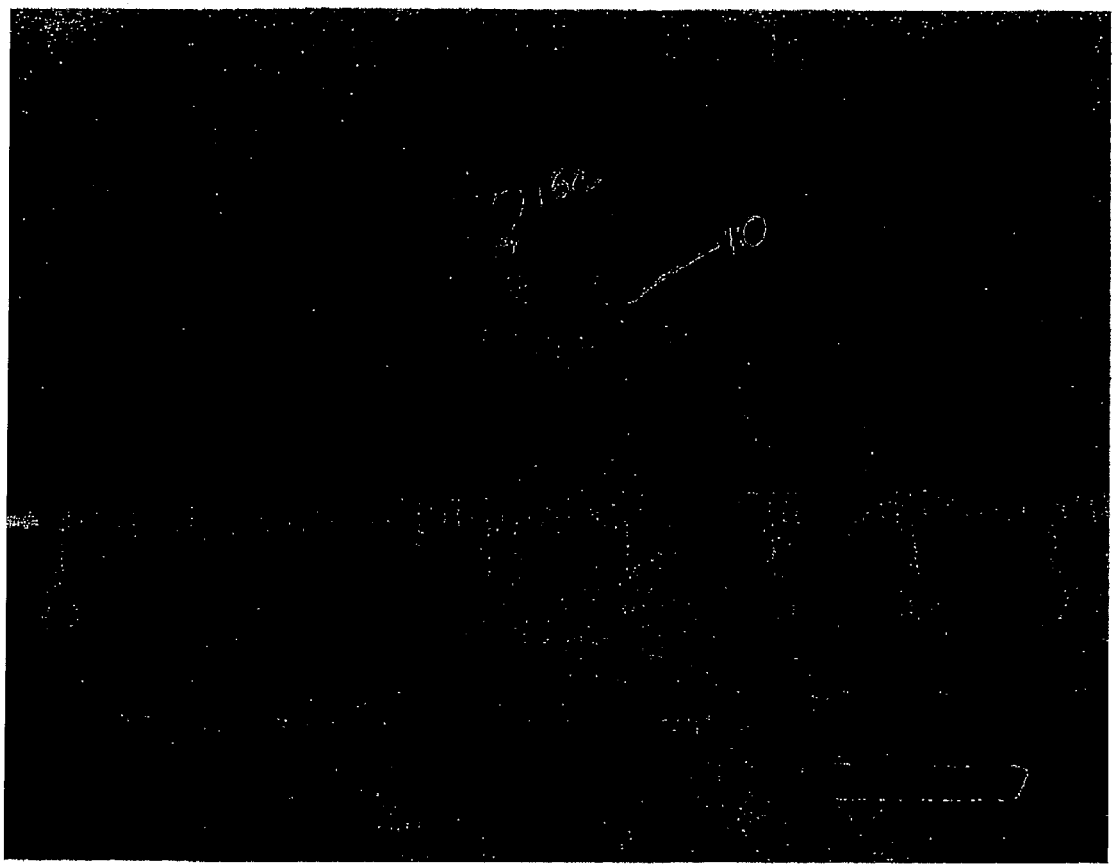
FIG. 18 is a digital image of a prototype RF resonator according to embodiments of the present invention.
Figure 19A:
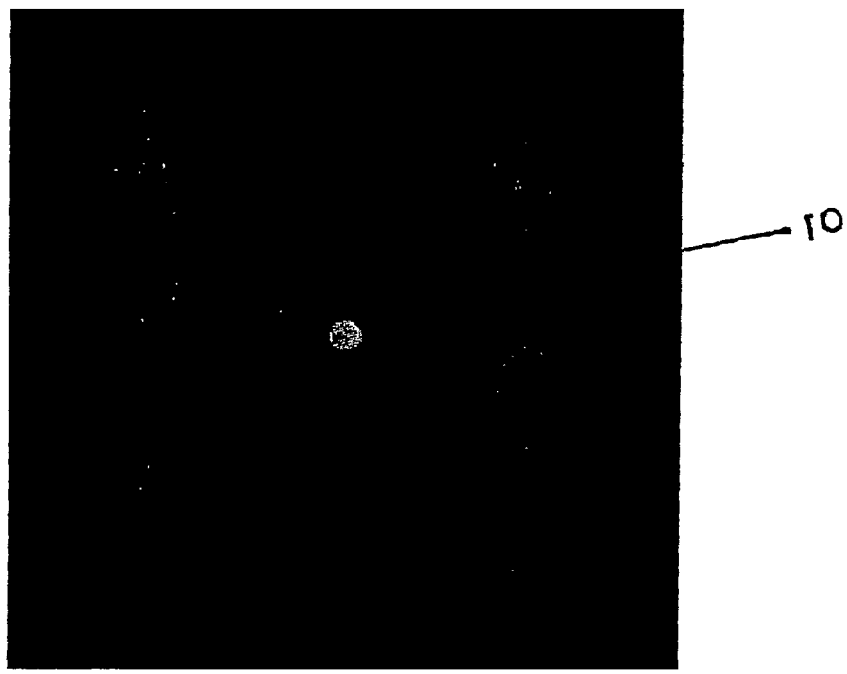
FIGS. 19A and 19B are MRI images obtained using signal data from the RF resonator shown in FIG. 18, when placed in a saline bath.
Figure 19B:

FIG. 18 is a digital image of a prototype RF resonator configured as a framing (generally spiraling) coiled body 15c. FIGS. 19A and 19B are MRI images (taken in a 1.5T system) of the device shown in FIG. 18 obtained with the device in a saline (phantom) bath. The region inside and outside the body 15c has increased SNR (shown as a brighter spot) relative to the other portions of the image.

Figure 20:
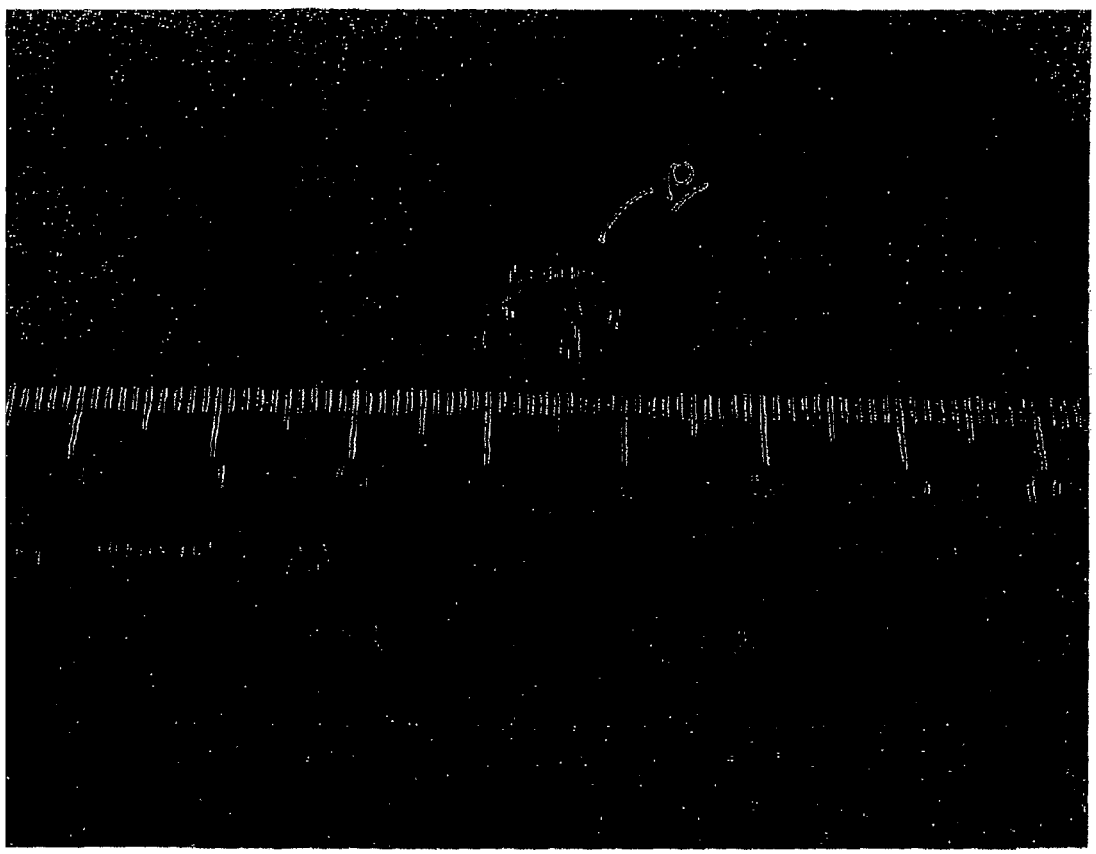
FIG. 20 is a digital image of an alternate prototype framing-member according to other embodiments of the present invention.
Figure 21A:
FIGS. 21A and 21B are MRI images are MRI images obtained using signal data from the RF resonator shown in FIG. 20, when placed in a saline bath.
Figure 21B:
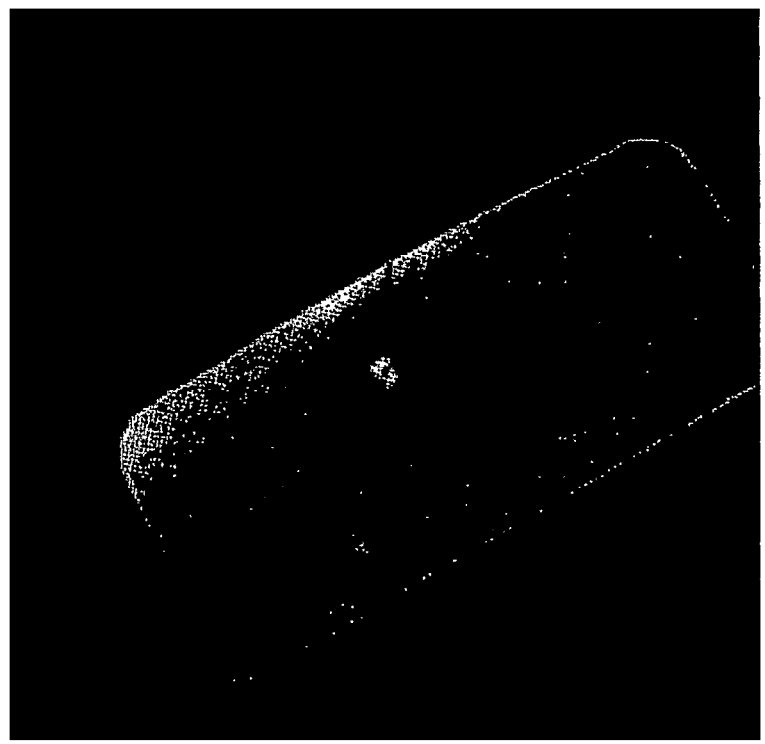

FIG. 20 illustrates another prototype RF resonator configured as a multi-lobe body that can occupy a generally spherical space. FIGS. 21A and 21B are MRI images of the device shown in FIG. 20 obtained with the device in a saline (phantom) bath. Again, the device location is illustrated by the brighter spot in the images, relative to the background. It is believed that the prototype coils generated about a three-fold improvement in SNR in the vicinity of the coil as compared to a conventional surface/head coil.

Figure 22:
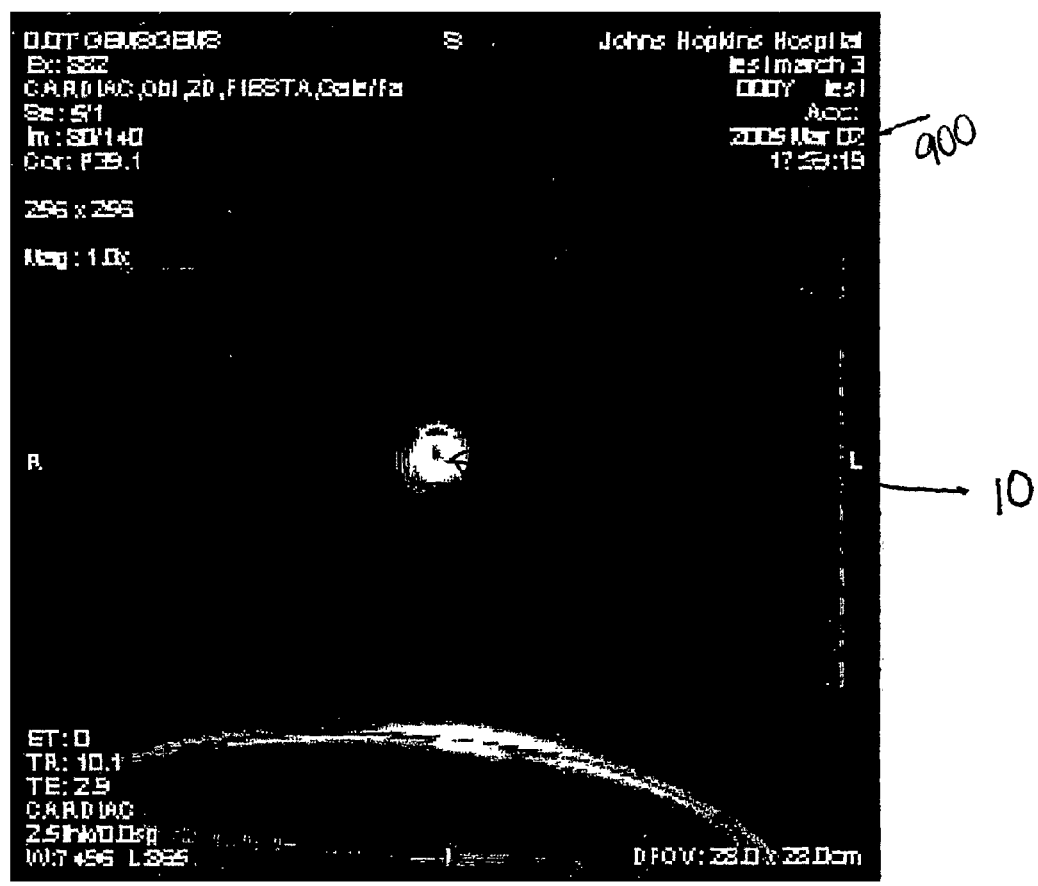
FIG. 22 is an MRI image illustrating a commercial coil and an RF resonator coil.

FIG. 22 is an MRI image illustrating a prototype MRI-visible RF resonator and a commercially available coil (the Cordis "Trufil" coil) indicated by arrow and feature 900.

Figure 23:
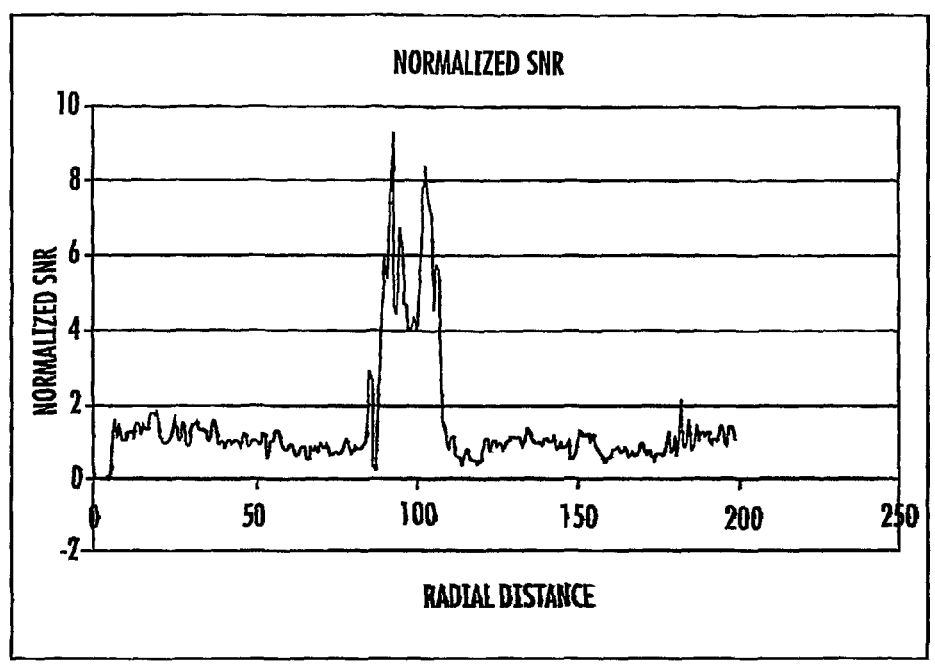
FIG. 23 is a graph of Normalized Signal to Noise Ratio (SNR) data versus radial distance (unitless) illustrating an SNR increase over conventional sac coils.

FIG. 23 is a graph of normalized SNR over radial distance that may be provided by RF resonators of the instant invention (s).

In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A first implantable device comprising: an implantable coil body configured and sized to reside in a sac of an aneurysm, wherein the implantable coil body has an inductance and capacitance, and wherein the capacitance is selected so that the implantable coil body resonates at a Larmor frequency of a predefined magnetic field strength in combination with a second implantable aneurysm-sac treatment device, the second device comprising a respective second implantable coil body configured and sized to reside in a sac of an aneurysm, wherein the second implantable coil body has an inductance and capacitance, and wherein the capacitance is selected so that the coil resonates at a Larmor frequency of a predefined magnetic field strength that is different from that of the first device.

2. An implantable device according to claim 1, wherein the first device resonates at 1.5 T and the second device resonates at one of the following: 2.0 T, 3.0 T, 6.0 T or 9.0 T.

3. An implantable device comprising: an implantable coil body configured and sized to reside in a sac of an aneurysm, wherein the implantable coil body has an inductance and capacitance, and wherein the capacitance is selected so that the implantable coil body resonates at a Larmor frequency of a predefined magnetic field strength, further comprising: a plurality of microcoils, at least two of which are configured with a different capacitance that is selected for operation at different magnetic field strengths of high-field MRI systems.

4. The implantable device of claim 3, wherein said device is useful for vascular occlusion.

* * * * *